(12) United States Patent
Kaestle et al.

(10) Patent No.: US 7,923,028 B2
(45) Date of Patent: Apr. 12, 2011

(54) HIGH DOSE ORAL FORMULATION OF BISPHOSPHONATE AND A PROCESS FOR MAKING THEREOF

(75) Inventors: Hans-G. Kaestle, Buggingen (DE); Bernard Meyer, Dietwiller (FR)

(73) Assignee: Hoffman-La Roche Inc., Nutley, NJ (US)

( * ) Notice: Subject to any disclaimer, the term of this patent is extended or adjusted under 35 U.S.C. 154(b) by 1039 days.

(21) Appl. No.: 10/639,010

(22) Filed: Aug. 12, 2003

(65) Prior Publication Data

US 2004/0121007 A1 Jun. 24, 2004

(30) Foreign Application Priority Data

Dec. 20, 2002 (EP) .................................. 02028745

(51) Int. Cl.
*A61K 9/20* (2006.01)
*A61K 9/28* (2006.01)
(52) U.S. Cl. ........................................ 424/474; 424/464
(58) Field of Classification Search ........................ None
See application file for complete search history.

(56) References Cited

U.S. PATENT DOCUMENTS

| | | |
|---|---|---|
| 3,962,432 A | 6/1976 | Schmidt-Dünker |
| 4,054,598 A | 10/1977 | Blum et al. |
| 4,073,838 A | 2/1978 | Barnickel et al. |
| 4,267,108 A | 5/1981 | Blum et al. |
| 4,327,039 A | 4/1982 | Blum et al. |
| 4,407,761 A | 10/1983 | Blum et al. |
| 4,621,077 A | 11/1986 | Rosini et al. |
| 4,624,947 A | 11/1986 | Blum et al. |
| 4,666,895 A | 5/1987 | Bosies et al. |
| 4,705,651 A | 11/1987 | Staibano |
| 4,711,880 A | 12/1987 | Stahl et al. |
| 4,719,203 A | 1/1988 | Bosies et al. |
| 4,746,654 A | 5/1988 | Breliere et al. |
| 4,761,406 A | 8/1988 | Flora et al. |
| 4,777,163 A | 10/1988 | Bosies et al. |
| 4,812,311 A | 3/1989 | Uchtman |
| 4,876,248 A | 10/1989 | Beliere et al. |
| 4,922,007 A | 5/1990 | Kieczykowski et al. |
| 4,927,814 A | 5/1990 | Gall et al. |
| 4,939,130 A | 7/1990 | Jaeggi et al. |
| 4,970,335 A | 11/1990 | Isomura et al. |
| 4,971,958 A | 11/1990 | Bosies et al. |
| 5,002,937 A | 3/1991 | Bosies et al. |
| 5,018,651 A | 5/1991 | Hull et al. |
| 5,019,651 A | 5/1991 | Kieczykowski |
| 5,206,253 A | 4/1993 | Bosies et al. |
| 5,344,825 A | 9/1994 | Khanna et al. |
| 5,348,748 A * | 9/1994 | Sheth et al. ................... 424/494 |
| 5,356,887 A | 10/1994 | Brenner |
| 5,358,941 A | 10/1994 | Bechard et al. |
| 5,431,920 A | 7/1995 | Bechard |
| 5,462,932 A | 10/1995 | Brenner et al. |
| 5,488,041 A | 1/1996 | Barbier et al. |
| 5,882,656 A | 3/1999 | Bechard et al. |
| 5,994,329 A | 11/1999 | Daifotis et al. |
| 6,123,964 A * | 9/2000 | Asgharnejad et al. ........ 424/489 |
| 6,124,314 A * | 9/2000 | Cameron et al. .............. 514/307 |
| 6,143,326 A | 11/2000 | Mockel et al. |
| 6,165,513 A | 12/2000 | Dansereau et al. |
| 6,294,196 B1 * | 9/2001 | Gabel et al. ................... 424/464 |
| 6,419,955 B1 | 7/2002 | Gabel et al. |
| 6,432,932 B1 | 8/2002 | Daifotis et al. |
| 6,468,559 B1 * | 10/2002 | Chen et al. ................... 424/451 |
| 6,544,967 B2 | 4/2003 | Daifotis et al. |
| 6,573,252 B1 | 6/2003 | Del Soldato |
| 6,638,920 B2 | 10/2003 | Thompson |
| 6,680,307 B1 | 1/2004 | Bauss et al. |
| 6,692,764 B2 | 2/2004 | Katdare et al. |
| 6,699,850 B2 | 3/2004 | Reszka et al. |
| 6,770,289 B2 | 8/2004 | Uria |
| 6,838,584 B2 | 1/2005 | Blizzard et al. |
| 6,991,806 B1 * | 1/2006 | Dickinson et al. ............ 424/464 |
| 7,008,640 B2 * | 3/2006 | Watanabe et al. ............ 424/458 |
| 2001/0051616 A1 | 12/2001 | Karpf et al. |
| 2002/0006441 A1 | 1/2002 | Gabel et al. |
| 2003/0118634 A1 | 6/2003 | Schofield et al. |
| 2003/0139378 A1 | 7/2003 | Daifotis et al. |
| 2003/0175340 A1 | 9/2003 | McCallister et al. |
| 2003/0195171 A1 | 10/2003 | Daifotis et al. |
| 2003/0225039 A1 | 12/2003 | Bauss et al. |
| 2004/0087550 A1 | 5/2004 | Zanetti et al. |
| 2004/0097469 A1 | 5/2004 | Little et al. |
| 2004/0147484 A1 | 7/2004 | Boyd et al. |
| 2005/0070504 A1 | 3/2005 | Burgio, Jr. et al. |

FOREIGN PATENT DOCUMENTS

CA 2308532 12/2000

(Continued)

OTHER PUBLICATIONS

Ringe et al., Rheumatology (Oxford), 42(6):743-9 (2003) (PMID:12730532 Abstract).
Schimmer et al., Clin Ther., 25(1):19-34 (2003) (PMID:12637110 Abstract).
Body et al., Support Care Cancer, 10(5):399-407 (2002) (PMID:12136223 Abstract).
Bergner et al., Nephrol Dial Transplant, 17(7):1281-5 (2002) (PMID:12105253 Abstract).
Body et al., J. Clin. Oncol.,16(12):3890-9 (1998) (PMID:9850035 Abstract).
Mazess, Lunar News, pp. 1 and 23 (1996).
Mazess, Lunar News, pp. 1 and 31 (1996).
Quimby et al., J. Org. Chem., 32, pp. 4111-4114 (1967).
Rus, B.J., et al ,J. of Bone and Mineral Res., (2001) 16(10), pp. 1871-1878.

(Continued)

*Primary Examiner* — S. Tran
(74) *Attorney, Agent, or Firm* — George W. Johnston; Patricia S. Rocha-Tramaloni; David E. Wildman

(57) ABSTRACT

The invention relates to a high dose oral formulation of bisphosphonates and to a process for the preparation of such formulations.

6 Claims, No Drawings

FOREIGN PATENT DOCUMENTS

| | | |
|---|---|---|
| CA | 2149052 | 3/2003 |
| EP | 336 298 | 10/1989 |
| EP | 558 913 | 9/1993 |
| EP | 1135140 B1 | 8/2005 |
| FR | 2797185 A1 * | 9/2001 |
| GB | 2 153 225 | 8/1985 |
| WO | WO 90/00798 | 1/1990 |
| WO | WO 9412200 A1 * | 6/1994 |
| WO | WO 96/09056 | 3/1996 |
| WO | WO 96/17616 | 6/1996 |
| WO | WO 97/15191 | 5/1997 |
| WO | WO 97/39755 | 10/1997 |
| WO | WO 99/09995 | 3/1999 |
| WO | WO 00/21450 | 4/2000 |
| WO | WO 00/21541 | 4/2000 |
| WO | WO 00/61111 | 10/2000 |
| WO | WO 01/01991 A1 | 1/2001 |
| WO | WO 0101991 A1 * | 1/2001 |
| WO | WO 01/15703 | 3/2001 |
| WO | WO 01/76592 A1 | 10/2001 |
| WO | WO 01/89494 A2 | 11/2001 |
| WO | WO 01/89494 A3 | 11/2001 |
| WO | WO 01/97788 A2 | 12/2001 |
| WO | WO 01/97788 A3 | 12/2001 |
| WO | WO 02/00204 | 1/2002 |
| WO | WO 02/03976 | 1/2002 |
| WO | WO 03/095029 | 11/2003 |
| WO | WO 2004/067063 | 8/2004 |

OTHER PUBLICATIONS

Delmas, P.D. et al, Calcified Tissue Intern (2003) 72(4), p. 332.
Chapurlat, R.D., et al, Expert Opinion on Pharmacotherapy, England (2003) 4(3), pp. 391-396.
Hyldstrup et al., Calcif Tissue Int., 53, pp. 297-300 (1993).
Nies, A.S., and Spielberg, S.P., Principles of Therapeutics, In Hardman, J.G., and L.E. Limbird (Eds.), Goodman & Gilman's the pharmacological basis of therapeutics, ninth edition, pp. 43-62, New York: McGraw-Hill (1996).
Bauss, et al., J. Rheumatol., 29, pp. 990-998 (2002).
Farmacia Remington, Chapter 76—Preformulation, 17 edition, 1987.
Giron, D., Journal of Thermal Analysis and Calorimetry, vol. 64, Budapest-2001, pp. 38.
Giron, D., Thermochimica Acta 248-1-59, Elsevier Science B.V., 1995, pp. 1-59.
Merck & Co., NJ, USA Merck Index $13^{th}$, 2001, No. 4899.
Pharmaceutical Dosage Forms, $2^{nd}$ Edition, 1989, vol. 1, pp. 34.
Hyldstrup L et al, *Calcified Tissue International*, (1993) 53(5), 297-300.
Excerpt on "Cellulose", Merck Index, $13^{th}$ Edition, pp. 1977 (2001).
Excerpt on "Starch", Merck Index, $13^{th}$ Edition, pp. 8877, (2001).
Remington's Pharmaceutical Sciences, $18^{th}$ Edition (1990).
Teva Opposition to EP 1596870, May 8, 2008.
Generics Opposition to EP 1596870, May 8, 2008.
Synthon Opposition to EP 1596870, May 8, 2008.
Banker et al., Modern Pharmaceutics, $4^{th}$ Ed., pp. 293-312 (2002).
Remington, The Science and Practice of Pharmacy, $20^{th}$ Ed., pp. 860-869 (2000).
Banker et al., Modern Pharmaceutics, $4^{th}$ Ed., p. 320-322 (2002).
Excerpt on "Ibandronic Acid", Merck Index, $14^{th}$ Ed. (2006).
Test Data, Nov. 3, 2006.
Excerpt on "Starch" and "Pregelatinized Starch", Handbook of Pharmaceutical Excipients, 3d Edition, pp. 522, 528 (2000).
Gordon et al, *Journal of Pharmaceutical Sciences*, k82;2 (1993)220-226.
Merck Index $14^{th}$ ed, (2001) p. 337 "Cellulose".
Banker G.S. et al, *Modern Pharmaceutics*, $4^{th}$ ed. (2002) 293-294, 297-298.
*Remington: The Science and Practice of Pharmacy*, $20^{th}$ ed. (2000) 860-865.
Sawbrick, J. et al, *Encyclopedia of Pharmaceutical Technology*, $2^{nd}$ ed. (2002) p. 2721.

* cited by examiner

HIGH DOSE ORAL FORMULATION OF BISPHOSPHONATE AND A PROCESS FOR MAKING THEREOF

FIELD OF THE INVENTION

The invention relates to a pharmaceutical composition for oral application consisting of a high dose of bisphosphonates or pharmaceutically acceptable salts thereof as active substance and to a process for the preparation of such compositions.

BACKGROUND OF THE INVENTION

Aminoalkyl-1,1-diphosphonic acid derivatives (hereinafter called by the general term bisphosphonates) are important pharmaceutical agents in the treatment of bone diseases and some disturbances of calcium metabolism such as hypercalcaemia, osteoporosis, tumor osteolysis, Paget's disease, etc.

Bisphosphonates as pharmaceutical agents are described, for example, in EP-A-170,228; EP-A-197,478; EP-A-22,751; EP-A-252,504; EP-A-252,505; EP-A-258,618; EP-A-350,002; EP-A-273,190; and WO-A-90/00798, each of which are incorporated herein by reference.

Pharmaceutical forms of currently marketed bisphosphonates are oral formulations (tablets or capsules) or solutions for intravenous injection or infusion. They are systemically well-tolerated when administered at therapeutic doses. However, bisphosphonates as a class are irritant to skin and mucous membranes, and when given orally on a continuous basis, may result in digestive tract side effects, e.g., esophageal adverse events or gastrointestinal disturbances. As a consequence, and due to their low oral bioavailability, the oral route of administration has, to date, to follow inconvenient recommendations of use for the patient.

As described, bisphosphonates are accepted as providing strong efficacy in the management of osteoporosis. However, given the administration restrictions related to low oral bioavailability and potential for gastrointestinal side effects, there is a clear opportunity for regimens which offer improved convenience and flexibility, leading to a higher level of compliance and superior patient management/satisfaction.

Furthermore, it has been found in the ibandronate clinical development program, that ibandronate showed fracture reduction efficacy with a drug-free interval beyond daily administration. It was quite unexpected that fracture reduction benefit could be derived from a weekly or monthly administration of an oral bisphosphonate with a single or multiple tablet administration scheme.

SUMMARY OF THE INVENTION

Accordingly, a new composition comprising a high dose, namely up to 250 mg, preferably comprising 150 mg or 100 mg of a bisphosphonate derivative, especially of ibandronate or pharmaceutically acceptable salts thereof was prepared, which on the one hand has an increased ratio of active substances versus excipients, and on the other hand fulfills the requirements of stability.

It has been found that the stability of such high dose formulations is substantially increased by adding the disintegrant already in the granulation step together with the active substance and with a part of the filler material. Such compositions are easily dissolvable and have an increased stability on storage both with regard to temperature and humidity.

The pharmaceutical composition according to the invention comprises up to 250 mg, preferably up to 200 mg, more preferably up to 150 mg, and most preferably up to 100 mg of a bisphosphonate, especially of ibandronate or a pharmaceutically acceptable salt thereof as an active substance. The following bisphosphonates are active substances which can be used in the pharmaceutical compositions according to the invention in the form of free acids or pharmaceutically acceptable salts or hydrates, particularly sodium salts:

(4-amino-1-hydroxybutylidene)bis-phosphonate (alendronate),
(dichloromethylene)bis-phosphonate (clodronate),
[1-hydroxy-3-(1-pyrrolidinyl)-propylidene]bis-phosphonate (EB-1053),
(1-hydroxyethylidene)bis-phosphonate (etidronate),
[1-hydroxy-3-(methyl pentyl amino)propylidene]bis-phosphonate (ibandronate),
[Cycloheptylamino)-methylene]bis-phosphonate (incadronate),
(6-amino-1-hydroxyhexylidene)bis-phosphonate (neridronate),
[3-(dimethylamino)-1-hydroxypropylidene]bis-phosphonate (olpadronate),
(3-amino-1-hydroxypropylidene)bis-phosphonate (pamidronate),
[1-hydroxy-2-(3-pyridinyl)ethylene]bis-phosphonate (risedronate),
[[(4-chlorophenyl)thiol]-methylene]bis-phosphonate (tiludronate),
[1-hydroxy-2-imidazo-(1,2-a)pyridin-3-yl ethylidene]bis-phosphonate (YH 529),
[1-hydroxy-2-(1H-imidazol-1-yl)ethylidene]bis-phosphonate (zoledronate); and
especially [1-hydroxy-3-(methyl pentyl amino)propylidene]bis-phosphonate (ibandronate).

These substances and their preparation are known and described, for example, in the following references: U.S. Pat. No. 4,705,651 (alendronate); U.S. Pat. No. 4,927,814 (ibandronate); U.S. Pat. Nos. 3,468,935; 3,400,147; and 3,475,486 (etidronate); O. T. Quimby et al, J. Org. Chem. 32, 4111 (1967) (clodronate); U.S. Pat. No. 4,505,321 (risedronate); U.S. Pat. Nos. 4,134,969 and 3,962,432 (pamidronate); U.S. Pat. No. 5,130,304 (EB-1053); U.S. Pat. No. 4,970,335 (incadronate); Belgian Patent No. 885139 (neridronate); U.S. Pat. No. 4,054,598 (olpadronate); U.S. Pat. Nos. 4,746,654; 4,876,248 and 4,980,171 (tiludronate); U.S. Pat. No. 4,990,503 (YH 529) and U.S. Pat. No. 4,939,130 (zoledronate).

Preferred are compositions comprising the equivalent of 150 mg bisphosphonates or pharmaceutically acceptable salts thereof and compositions comprising the equivalent of 100 mg bisphosphonates or pharmaceutical acceptable salts as active substances, respectively. Ibandronate or a pharmaceutically acceptable salt thereof is a particularly preferred active substance, particularly in the form of sodium-ibandronate monohydrate.

The composition further comprises adjuvants such as binders, for example, polyvinylpyrrolidone (e.g., Povidone®) or hydroxypropylmethyl cellulose (e.g., Pharmacoat®), fillers, for example, lactose in hydrate or anhydrate form, cellulose in microcrystalline or fibrous form (e.g. Avicel®), or starch, disintegrants, for example, cross-linked polyvinyl pyrrolidone (e.g. Crospovidone® USPNF) or cross carmelose, lubricants, for example, stearic acid or magnesium stearate, and flow-regulators for example colloidal silicon dioxide.

The preferred form of the composition are tablets, preferably coated by a film coating mixture and a plastiziser. Such film coating mixtures and plasticizers are known to the person skilled in the art.

According to this invention, the tablet kernel consists of from about 30.0 to about 36.0 5, preferably of about 33.3.% of active substance;
of from about 4.0 to about 6.0%, preferably of from about 4.8 to about 5.2% by weight of binder;
of from about 39.6 to about 59.4%, preferably of from about 47.0 to about 52.0% by weight of filler;
of from about 4.5 to about 5.5%, preferably of from about 4.8 to about 5.2% by weight of disintegrant;
of from about 1.8 to about 2.2%, preferably of from about 1.9 to about 2.1% by weight of lubricant; and
of from about 0.9 to about 1.1%, preferably of from about 0.95 to about 1.05% by weight of flow regulator.

Preferably the active substance is ibandronate or a pharmaceutically acceptable salt thereof; preferably, the binder is polyvinylpyrrolidone; preferred fillers are lactose in hydrate or anhydrate form, or cellulose in microcrystalline or fibrous form; and a preferred disintegrant is cross-linked polyvinyl pyrrolidone. Preferred are compositions wherein the disintegrant is added already in the granulate together with the active substance and with a part of the filler material.

Furthermore, the invention relates to a process for the preparation of pharmaceutical compositions for the oral application comprising a high dose of bisphosphonates, especially of ibandronate or a pharmaceutically acceptable salt thereof. According to the invention, the pharmaceutical composition is prepared by the following process:
  wet granulating the bisphosphonate or pharmaceutically acceptable salt thereof in the presence of adjuvants such as the binder, and a part of fillers mentioned above, characterized in that the disintergrant is added into the granulation mixture;
  fluidizing the granulation mixture in a manner known in the art;
  subsequently drying the wet granulate and screening the dried granulate through a screen having a suitable mesh width;
  adding the remaining adjuvants such as the fillers, lubricant and flow regulators mentioned above and blending the mixture before processing it by techniques known in the art to form pharmaceutical compositions.

In a preferred form of the invention, the active substance, a part of the filler, and the disintegrant in dry powder form are granulated by spraying an aqueous binder solution into the powder mixture. The process is preferably carried out at a temperature of 60 to 80° C., preferably at about 70° C.

The spray granulated material is then dried preferably at a temperature of 60 to 80° C., preferably at about 70° C. and subsequently screened through a fine sieve; the dried granulate is mixed with the remaining amount of the filler, the lubricant, and the flow regulator which were previously passed through a fine sieve. The final blend is then pressed into tablet kernels which are coated with a coating suspension using purified water and a film-coating mixture.

DETAILED DESCRIPTION OF THE INVENTION

The process according to the invention is carried out as follows:
a) dissolving the binder, preferably Povidone K25® in purified water;
b) charging a drier, preferably a fluid-bed drier with the bisphosphonate, preferably with the mono-sodium salt (1H$_2$O) of ibandronic acid, a part of the filler, preferably with lactose monohydrate and up to 60% by weight of the total amount of microcrystalline cellulose, and the disintegrant;
c) spray-granulating the raw materials of step b) at a temperature of from about 60 to about 80° C., preferably at about 70° C. with the granulation fluid of step a),
d) drying the spray granulated material of step c) at a temperature of 60 to 80° C., preferably at about 70° C. (setpoint of inlet-air temperature) and subsequently screening the dried intermediate through a fine sieve;
e) mixing the granulate of step e) with the remaining amount of the filler, e.g., microcrystalline cellulose, the lubricant, preferably stearic acid and the flow regulator, for example, anhydrous colloidal silica which were previously passed through a fine sieve (e.g., 1 mm);
f) compressing the final blend of f) into tablet kernels; and coating the tablet with a coating suspension using purified water and a film-coating mixture comprising for example hypromellose, titanium dioxide and talc (the mixture being commercially available, e.g. Opadry® 00A28646) and Macrogol 6000®.

The adjuvants are known in the art and are commercially available.

The invention will now be explained in further detail with reference to examples, without being limited thereto.

EXAMPLE 1

The preparation of a film coated tablet containing 150 mg active substance is carried out as follows:
1. Dissolve Povidone K25® in purified water.
2. Charge a fluid-bed drier with mono-sodium salt (1H$_2$O) of ibandronic acid, lactose monohydrate, crospovidone and microcrystalline cellulose. Crospovidone and the microcrystalline cellulose were passed through a fine sieve (e.g., 1 mm) before mixing.
3. Spray-granulate the raw materials of step 2 at 70° C. (set point of inlet-air temperature) with the granulation fluid of step 1.
4. Perform a final drying of the spray granulated material of step 3 at 70° C. (setpoint of inlet-air temperature).
5. Screen the dried intermediate granulate through a fine sieve (e.g., 2 mm perforations) and
6. If required, repeat steps 1-5 to obtain the required final batch size.
7. Mix the granulate of step 6 in a container mixer with microcrystalline cellulose, stearic acid and anhydrous colloidal silica. The microcrystalline cellulose, the stearic acid and the anhydrous colloidal silica were passed through a fine sieve (e.g., 1 mm) before mixing.
8. Compress the final blend from step 7 into tablet kernels using a rotary tablet press.
9. Prepare the coating suspension using purified water, film-coating mixture comprising hypromellose (60.5%), titanium dioxide (29%) and talc (10.5%); the mixture is purchased from the market (e.g. Opadry® 00A28646) and Macrogol 6000®.
10. Spray the coating suspension of step 9 onto the tablet kernels using a coating unit.

The tablet composition is as follows:

| Tablet kernel | |
|---|---|
| Ibandronic acid | 150.0 mg |
| as mono-sodium salt (1H$_2$O) of Ibandronic acid | 168.75 mg |
| Povidone K25 ® | 22.5 mg |
| Lactose, monohydrate | 62.75 mg |
| Cellulose, microcrystalline | 60.0 mg |
| Crospovidone ® | 22.5 mg |
| Stearic acid | 9.0 mg |
| Silica, anhydrous colloidal | 4.5 mg |
| Film-coat | |
| Film-coating mixture* | 12.75 mg |
| Macrogol 6000 ® | 2.25 mg |

*this film-coating mixture contains: hypromellose (60.5%), titanium dioxide (29%) and talc (10.5%); the mixture is commercially available (e.g., Opadry ® 00A28646)

The kernel weight is 450 mg and the total tablet weight is 465 mg, the amount of active substance per tablet is equivalent to 150 mg of free ibandronic acid.

Example 1a

For a Batch of 110,000 Tablets

1. A suitable vessel was charged with 14.850 kg demineralized water and 2.475 kg of Povidone K25® was added under constant stirring. The time of addition was about 15 minutes.
2. A fluid-bed dryer was charged with 18.563 kg ibandronic acid mono sodium salt, 17.903 kg of lactose monohydrate 100, 4.125 kg Avicel PH-102® and 2.475 kg Crospovidone CL®.
3. The components were mixed and spray granulated at a temperature of 70° C. with the aqueous solution of Povidone K25® prepared above which was added at 300 g/min with a pressure of 2.5 bar.
4. The granulate was then dried in a fluid-bed dryer at 70° C.
5. Subsequently screened (2.0 mm meshes) to yield 44.540 kg of dried granulated material.
6. 2.426 kg AVICEL PH-102®, 0.970 kg stearic acid and 0.4850 kg silicic acid AEROSIL 200% were screened and added to the dried granulated material (44.650 kg), and the components were mixed.
7. The final blend was compressed into tablets kernels, yield 103,244 kernels.
8. A coating suspension was prepared by dissolving 0.290 kg PEG 6000® (MACROGOL 6000) in 7.743 kg demineralized water and subsequently dispersing 1.645 kg OPADRY 00A28646® into this solution.
9. The kernels were coated with the coating suspension under standard conditions.

The tablets have the composition and the weight given in example 1.

EXAMPLE 2

The preparation of a film coated tablet containing 100 mg active substance was carried out as described in example 1:

| Tablet kernel | |
|---|---|
| Ibandronic acid | 100.0 mg |
| as mono-sodium salt (1H$_2$O) of Ibandronic acid | 112.50 mg |
| Povidone K25 ® | 15.0 mg |
| Lactose, monohydrate | 108.50 mg |
| Cellulose, microcrystalline | 40.0 mg |
| Crospovidone ® | 15.0 mg |
| Stearic acid | 6.0 mg |
| Silica, anhydrous colloidal | 3.0 mg |
| Film-coat | |
| Film-coating mixture* | 10.20 mg |
| Macrogol 6000 ® | 1.80 mg |

*composition as mentioned example 1

The kernel weight is 300 mg and the total tablet weight is 312 mg, the amount of active substance per tablet is equivalent to 100 mg of free ibandronic acid.

What is claimed is:

1. A process for the preparation of a tablet comprising ibandronic acid or a pharmaceutically acceptable salt thereof and a disintegrant, wherein the disintegrant is selected from the group consisting of crosslinked polyvinylpyrrolidone and croscarmellose, comprising
    a) spray-granulating ibandronic acid or a pharmaceutically acceptable salt thereof, filler and the entire amount of the disintegrant to be used in the preparation of the tablet with a solution of a binder in purified water at a temperature of about 70° C. to yield a spray granulated material;
    b) drying the spray granulated material at a temperature of about 70° C. and subsequently screening the dried spray granulated material through a fine sieve;
    c) mixing the dried spray granulated material with a mixture consisting of additional filler, a lubricant, and a flow regulator wherein said mixture was previously passed through a fine sieve, to yield a final blend; and
    d) compressing the final blend into tablet kernels.
2. A process according to claim 1, comprising
    a) dissolving the binder in purified water to provide a granulation fluid;
    b) charging a fluid bed drier with the ibandronic acid or a pharmaceutically acceptable salt thereof, the first portion of the filler, and the disintegrant;
    c) spray-granulating the filler, disintegrant, and ibandronic acid or a pharmaceutically acceptable salt thereof of step b) at a temperature of about 70° C. with the granulation fluid of step a) in the fluid bed drier to yield a spray granulated material;
    d) drying the spray granulated material of step c) at a temperature of about 70° C. and subsequently screening the dried spray granulated material through a fine sieve;
    e) mixing the dried spray granulated material of step d) in a mixer with the second portion of the filler, the lubricant, and the flow regulator which were previously passed through a fine sieve to yield a final blend; and
    f) compressing the final blend of e) into tablet kernels.
3. The process according to claim 2, wherein the bisphosphonate is the monosodium salt, monohydrate of ibandronic acid.
4. The process according to claim 3, wherein the disintegrant is crosslinked polyvinylpyrrolidone.
5. The process according to claim 2, further comprising coating the kernels with a coating suspension comprising purified water and a film coating mixture.
6. The process according to claim 4, further comprising coating the kernels with a coating suspension comprising purified water and a film coating mixture.

* * * * *